(12) United States Patent
Hug et al.

(10) Patent No.: US 12,400,775 B2
(45) Date of Patent: Aug. 26, 2025

(54) SYNTHETIC ANTIFERROMAGNET DISK-SHAPED PARTICLE AND SUSPENSION COMPRISING SUCH PARTICLES

(71) Applicants: Empa, Swiss Federal Laboratories for Materials Science and Technology, Düebendorf (CH); Universitaet Wien, Vienna (AT)

(72) Inventors: Hans Josef Hug, Kirchdorf (CH); Dieter Suess, Vienna (AT)

(73) Assignee: Empa, Swiss Federal Laboratories for Materials Science and Technology, Düebendorf (CH)

( * ) Notice: Subject to any disclaimer, the term of this patent is extended or adjusted under 35 U.S.C. 154(b) by 0 days.

(21) Appl. No.: 18/255,089

(22) PCT Filed: Nov. 30, 2021

(86) PCT No.: PCT/EP2021/083572
§ 371 (c)(1),
(2) Date: May 30, 2023

(87) PCT Pub. No.: WO2022/117564
PCT Pub. Date: Jun. 9, 2022

(65) Prior Publication Data
US 2024/0029927 A1      Jan. 25, 2024

(30) Foreign Application Priority Data
Dec. 1, 2020 (EP) .................................... 20211045

(51) Int. Cl.
*H01F 1/00*      (2006.01)
*A61K 41/00*     (2020.01)

(52) U.S. Cl.
CPC ....... *H01F 1/0054* (2013.01); *A61K 41/0052* (2013.01)

(58) Field of Classification Search
None
See application file for complete search history.

(56) References Cited

U.S. PATENT DOCUMENTS 6,303,218 B1 * 10/2001 Kamiguchi ......... H01F 10/3268
  428/816
6,337,215 B1    1/2002 Wilson
  (Continued)

FOREIGN PATENT DOCUMENTS

EP      0919285 A2     6/1999

OTHER PUBLICATIONS

Ackermann, Michel S et al: "Switching of biaxial synthetic antiferromagnets: A micromagnetic study", Journal of Applied Physics 124: 223901 (2018).

(Continued)

*Primary Examiner* — Ronak C Patel
(74) *Attorney, Agent, or Firm* — Merchant & Gould P.C.

(57) ABSTRACT

The synthetic antiferromagnet disk-shaped particle comprises a first ferromagnetic layer, a second ferromagnetic layer and a non-magnetic interlayer arranged between the first and the second ferromagnetic layer, wherein each of the first and the second ferromagnetic layer comprises a uniaxial magnetic anisotropy in the plane of the ferromagnetic layers such that the switching fields from an antiferromagnetic alignment of the first and the second ferromagnetic layer to a ferromagnetic alignment ($H_{AF \to F}$) and from the ferromagnetic alignment to the antiferromagnetic alignment ($H_{F \to AF}$) fulfill the condition $$H_{AF \to F} - H_{F \to AF} > \frac{1}{4} \cdot H_{AF \to F}.$$

16 Claims, 3 Drawing Sheets

(56) References Cited

U.S. PATENT DOCUMENTS

| | | |
|---|---|---|
| 6,721,141 B1 | 4/2004 | Attenborough et al. |
| 2008/0206891 A1* | 8/2008 | Wang ................ G01N 33/5434 436/526 |
| 2009/0273965 A1* | 11/2009 | Takenaga ............ G11C 11/1657 365/158 |
| 2013/0052343 A1 | 2/2013 | Dieny et al. |

OTHER PUBLICATIONS

Fallarino, Lorenzo et al: "Magnetic field induced switching of the antiferromagnetic order parameter in thin films of magnetoelectric chromia", Physical Review B 91, 054414 (2015).

Kita, Eiji et al: "Hysteresis Power-Loss Heating of Ferromagnetic Nanoparticles Designed for Magnetic Thermoablation", IEEE Transactions on Magnetics 44(11): 4452-4455 (2008).

Dennis Cindi L. et al: "Physics of heat generation using magnetic nanoparticles for hyperhermia", International Journal of Hyperthemia 29(8): 715-729 (2013).

International Search Report and Written Opinion for PCT/EP2021/083572 (Feb. 4, 2022).

\* cited by examiner

SYNTHETIC ANTIFERROMAGNET DISK-SHAPED PARTICLE AND SUSPENSION COMPRISING SUCH PARTICLES

This application is a US National Stage application of PCT International patent application No. PCT/EP2021/083572, filed Nov. 30, 2021, which claims the benefit of priority to European Patent Application No. 20211045.8, filed Dec. 1, 2020, which applications are incorporated herein by reference. To the extent appropriate, a claim of priority is made to each of the above disclosed applications.

The invention relates to a synthetic antiferromagnet disk-shaped particle and a suspension comprising such particles, in particular for hyperthermia application.

Magnetic hyperthermia is a technique to thermally ablate or destroy cells of a tumor by heat arising from magnetization losses of magnetic particles located in an oscillating magnetic field. Alternatively, a drug comprised in a suitably functionalized particle can be released by the heat generated from magnetization losses of the particles.

For hyperthermia applications typically superparamagnetic particles are used. Their vanishing magnetization in zero magnetic field permits the formation of a stable suspension of the particles in liquids. Because of their superparamagnetic characteristics only a small hysteresis develops when an oscillatory external magnetic field with a sufficiently high oscillation frequency f and field amplitude H is applied. However, the product of frequency and field amplitude must be kept below a biological discomfort level such that heating of the surrounding tissue by eddy currents is kept at an acceptably small level. For hyperthermia applications the biological discomfort level has been defined as $H \cdot f < 5 \cdot 10^9$ $Am^{-1}s^{-1}$ (H times f smaller than $5 \cdot 10^9$ A/m per second). Consequently, the specific heating power of the currently used superparamagnetic particles (Watts per gram) is small. This limits the temperature rise achievable by such particles injected into tumors embedded in surrounding body tissue, and thus the potential of such particles to thermally destroy the tumor.

It is therefore desirable to have magnetic particles with improved heating efficiency (higher Watts per gram). It is further desirable to have magnetic particles forming stable particles suspensions. It is yet further desirable to have a synthetic antiferromagnet particle with improved heating properties in external magnetic fields below a biological discomfort level and vanishing magnetization in zero external magnetic field.

According to the invention, there is provided a disk-shaped synthetic antiferromagnet particle comprising a first ferromagnetic layer, a second ferromagnetic layer and a non magnetic interlayer arranged between the first and the second ferromagnetic layer. Each of the first and the second ferromagnetic layer of the particle comprises a uniaxial magnetic anisotropy in the plane of the ferromagnetic layer such that switching fields from an antiferromagnetic alignment of the first and the second ferromagnetic layer to a ferromagnetic alignment ($H_{AF \to F}$) of the first and the second ferromagnetic layer and from the ferromagnetic alignment of the first and the second ferromagnetic layer to the antiferromagnetic alignment ($H_{F \to AF}$) of the first and the second ferromagnetic layer fulfill the condition $$H_{AF \to F} - H_{F \to AF} > \frac{1}{4} \cdot H_{AF \to F}.$$

Preferably, the switching fields fulfil the condition $$H_{AF \to F} - H_{F \to AF} > \frac{1}{2} \cdot H_{AF \to F},$$

more preferably $$H_{AF \to F} - H_{F \to AF} > \frac{1}{1.01} \cdot H_{AF \to F} \text{ or}$$

$$H_{AF \to F} - H_{F \to AF} > 1.99 \cdot H_{AF \to F}.$$

These conditions may be measured, for example, by vibrating sample magnetometry. As hysteretic effects are temperature dependent, in particular in small particles, measurements are performed at room temperature. These switching fields are measured on a time scale typical for vibrating sample magnetometry. Preferably, these field conditions also exist when measured on a time scale of 10 μs.

The field $H_{AF \to F}$ is always positive. The field $H_{F \to AF}$ can also be negative. According to a simple Stoner-Wohlfarth model, for the disk-shaped synthetic antiferromagnet particle, the switching fields are related to a uniaxial anisotropy in the plane of the ferromagnetic layers that is given by $$H_{AF \to F} = \alpha(T, V, M_s) \cdot \left( \frac{2K_u}{\mu_0 M_S} + \frac{j_{int}}{t\mu_0 M_S} \right) \text{ and } H_{F \to AF} = -\alpha(T, V, M_s) \cdot \left( \frac{2K_u}{\mu_0 M_S} + \frac{J_{int}}{t\mu_0 M_S} \right).$$

Therein, $K_u$ is the uniaxial anisotropy in the plane of the layers, $M_s$ is the saturation magnetization of the ferromagnetic layer, t is the thickness of the ferromagnetic layer, and $J_{int}$ is the coupling energy per surface areas between the ferromagnetic layers. $\alpha(T, V, M_s)$ is a parameter between 0 and 1 that depends on the temperature T, $M_s$, and the particle volume V. The temperature dependence can be approximated by Sharocks' equation. At zero temperature and neglecting the demagnetization effects $\alpha=1$.

Preferably, the switching field $\mu_0 H_{AF \to F}$ is between 5 mT and 200 mT.

Each of the first and the second ferromagnetic layer of the particle preferably comprises a uniaxial magnetic anisotropy in the plane of the ferromagnetic layers of at least 5000 Joule per cubic meter.

Preferably, the ferromagnetic layers each have a magnetic anisotropy between 10 Kilojoule per cubic meter and 200 Kilojoule per cubic meter. Preferably the magnetic anisotropy is at least 20 Kilojoule per cubic meter.

The uniaxial magnetic anisotropy in the plane of the ferromagnetic layers must be sufficiently large to align the magnetic moments within each ferromagnetic layer to achieve a layer magnetization M as close as possible to a saturation magnetization $M_s$ of the layer. Preferably, the uniaxial magnetic anisotropy in the plane of each ferromagnetic layer is as large in order to achieve a layer magnetization M of at least $0.7 M_s$, more preferably $M > 0.8 \cdot M_s$, even more preferably $M > 0.9 \cdot M_s$, for example $0.95 M_s$. Preferably, an anisotropy field, $H_K$ is achieved such that $\mu_0 H_K$ is between 10 and 200 millitesla.

The uniaxial magnetic anisotropy of the first ferromagnetic layer and the uniaxial magnetic anisotropy of the second ferromagnetic layer may have a same value or substantially a same value or may be different. Preferably, the magnetic anisotropy of the first ferromagnetic layer and of the second ferromagnetic layer has a same value or substantially a same value.

'Substantially same values' of anisotropy may, for example, deviate from an exact value by about 10 percent. Variations in anisotropy may be based on manufacturing or geometric tolerances. Different anisotropy in the first and the second ferromagnetic layer is preferably created upon manufacturing the particle. For example, upon choosing different deposition parameters when manufacturing a ferromagnetic layer, different anisotropy values in a layer may be created.

Preferably, a synthetic antiferromagnet particle has an antiferromagnetic ground state in zero applied magnetic field with vanishing total magnetization. The first and the second ferromagnetic layers each have a uniaxial anisotropy in the plane of the layers aligning their magnetic moment directions along this axis preferably resulting in a magnetization of the ferromagnetic layers close to the saturation value, preferably at least about 90 percent of the saturation value.

The coupling of the first and the second ferromagnetic layer is such that a stable ground state with an antiferromagnetic alignment of the two ferromagnetic layers is created.

Preferably, the synthetic antiferromagnet particle consisting of a pair of antiferromagnetically coupled ferromagnetic layers has no or a negligible permanent magnetic moment. A particle having a permanent magnetic moment, such as a ferromagnetic particle, would lead to an attractive inter particle interaction. This would lead to destabilization of a suspension of such particles in a liquid.

While the amount of anisotropy in the ferromagnetic layers of the particle may vary and may be varied with material selection, manufacturing method, layer thicknesses and particle geometry, the anisotropy is a prerequisite of hysteresis in ferromagnets.

Providing now an antiferromagnet particle with a minimum in-plane magnetic anisotropy of 5000 Joule per cubic meter, and the particle having its anisotropy axis aligned with the external field, the particle shows a hysteresis with hysteresis losses for heat generation sufficient for hyperthermia applications. The particles even show improved heat generation compared to existing particles for hyperthermia applications.

Synthetic antiferromagnet nanoparticles comprised of ferromagnetic layers are described in U.S. Pat. No. 6,337,215 B1. These particles comprise two ferromagnetic layers separated by a non-magnetic spacer layer such that the ferromagnetic layers are antiferromagnetically coupled. The particles may contain other layers consisting of antiferromagnetic materials to provide an exchange bias or to provide additional antiferromagnetic coupling between the two ferromagnetic layers. These particles are used for biological or medical applications such as cell separation or separation of molecules from liquids.

However, these particles are not suitable for hyperthermia applications where hysteresis losses in the particles are required for heat generation. The particles described in U.S. Pat. No. 6,337,215 B1 have no or only a negligible in-plane anisotropy. For this reason, for a field Y aligned along the magnetization axis of one of the ferromagnetic layers of the particle, the magnetization of the other ferromagnetic layer abruptly aligns to the field direction if a critical field value $H_{AF \to F}$ is surpassed. The magnetization switches back to the antiparallel direction at a field only slightly smaller than this critical field, namely at field condition $$H_{AF \to F} - H_{F \to AF} < \frac{1}{4} \cdot H_{AF \to F},$$

such that only a narrow hysteresis loop occurs (easy axis magnetization behaviour). In liquids, where the particles can rotate freely, the particles described in U.S. Pat. No. 6,337, 215 B1 rotate such that the magnetization directions of both ferromagnetic layers become perpendicular to the applied field. If the field is increased the magnetization directions of both ferromagnetic layers gradually rotate towards the field axis (hard axis magnetization behaviour) and a linear magnetization loop without hysteresis occurs. Accordingly, no or only very small hysteresis losses can be generated in these particles.

The particles of the present invention have ferromagnetic layers with a uniaxial anisotropy $K_u$ in the plane of the layers. For a field aligned along this uniaxial anisotropy axis the ferromagnetic layer with a magnetization opposite to the direction of the applied field shows an M(H)-loop with an area that is larger than $0.25\ M_s \cdot H_{AF \to F}$, preferably larger than $0.5\ M_s \cdot H_{AF \to F}$, more preferably larger than $0.8\ M_s \cdot H_{AF \to F}$ in the first quadrant of the M-H-coordinate system. The larger the area enclosed in the hysteresis loop, the larger the hysteresis losses and according heat generation in the synthetic antiferromagnet particle. The hysteresis loops are preferably measured with a time scale of 10 μs or at even larger time scales typical for vibrating sample magnetometry.

In general, a magnetization curve or a hysteresis loop of a material is represented in a coordinate system depicting the magnetization M of the material versus the applied magnetic field H. The first quadrant in this coordinate system of magnetization M versus magnetic field H refers to positive magnetic field H values and positive magnetization M values. The third quadrant refers to negative H values and negative M values. For a field $H > H_{AF \to F} > 0$ applied along the uniaxial anisotropy axis, the alignment of the magnetizations of the two ferromagnetic layers is essentially parallel, for example larger than $0.7 \cdot M_s$. When the field H is lowered towards zero, the alignment of two ferromagnetic layers again becomes antiparallel at a switching field $H_{F \to AF} > 0$, i.e. the magnetization orientation characteristic for a synthetic antiferromagnet is re-established if the applied magnetic field is removed.

For negative magnetic fields, the same magnetization process occurs such that a hysteresis loop occurs for the equivalent negative fields, and negative magnetization values, i.e. the M(H)-loop occurs in the third quadrant of the M-H-coordinate system.

The switching field $H_{AF \to F}$ is however usually smaller than the hard axis saturation field $H_s$.

Preferably, the synthetic antiferromagnet disk-shaped particle shows a magnetic hysteresis loop in externally applied magnetic fields μ₀H of 200 millitesla or smaller or preferably of 140 millitesla or smaller, preferably at external magnetic fields between 10 millitesla and 120 millitesla, more preferably between 5 millitesla and 50 millitesla.

Some embodiments of the particle show an almost perfect magnetization up to the magnetic saturation of the particle along its easy axis and almost perfect demagnetization into the antiferromagnetic ground state. In these embodiments of the particle, the particle is in its antiferromagnetic state when no magnetic field is applied.

Preferably, an area contained in the hysteresis loop is maximized in order to maximize the hysteresis losses.

Upon application of a (static) magnetic field the antiferromagnetic alignment of the ferromagnetic layers is switched to a ferromagnetic alignment. Upon oscillating the magnetic field, either between 0 and $H_{AF \to F}$ or between +H and −H with $H > H_{AF \to F}$, the particle is driven through its easy axis hysteresis loop in the first quadrant or in the first and third quadrant, and the ferromagnetic layers switch between antiferromagnetic and ferromagnetic alignment.

Preferably, the magnetic hysteresis loop has a substantially rectangular shape in the first and third quadrant in a coordinate system depicting magnetization versus magnetic field.

The hysteresis loops of the antiferromagnet particle preferably have the form of a rectangle in the first and in the third quadrant of the magnetization loop, however possibly including a small rounding at the edges of the rectangles. Small deviations from the exact rectangular shape represent imperfect magnetization or flattening saturation effects in the particle.

Preferably, the rectangular shape of the hysteresis loops is available also for particles comprising a remanence after having switched into the ferromagnetic alignment, thus for particles where the ferromagnetic layer does not switch back to the antiferromagnetic alignment of the two ferromagnetic layers when the field is ramped back from a value larger than $H_{AF \to F}$ to zero.

A negative field $-|H_{F \to AF}| < 0$ is then required to switch the magnetization of the one ferromagnetic layer back to a direction antiparallel to that of the other ferromagnetic layer. An oscillatory field applied along the uniaxial anisotropy axis with a field amplitude $H > H_{AF \to F}$ however still reverses the magnetizations of both ferromagnetic layers and thus leads to hysteretic losses. The area of the hysteresis loop is maximized if a negative field $-|H_{F \to AF}| < 0$ is required to switch the magnetization of the ferromagnetic layer back to a direction antiparallel to that of the other ferromagnetic laser, and $|H_{F \to AF}| \lesssim |H_{AF \to F}|$.

As mentioned above, a synthetic antiferromagnet particle with such properties does not switch back to the antiferromagnetically aligned state if the field is ramped down to zero. The particle would remain in the ferromagnetically aligned state, which would lead to a magnetostatic attraction between particles and consequently to a destabilization of a particle suspension. A synthetic antiferromagnet particle with such properties can be brought back into its antiferromagnetic alignment by an oscillatory field with a decaying magnitude. It may also be brought back into the antiferromagnetic alignment by thermal decay. When having a sufficiently small volume of the ferromagnetic layers and small uniaxial anisotropy, a thermally induced decay into the antiferromagnetic alignment occurs within a reasonable time, for example a time shorter than 10 seconds, shorter than 5 seconds or shorter than 1 second in zero field.

The anisotropy kept constant, the exchange coupling between the two layers is adjusted, preferably so that the energy barrier between the parallel state and the antiparallel state is preferably smaller than 25 $k_B T$, preferably smaller than 10 $k_B T$ or even smaller than 5 $k_B T$ at zero external field. This leads to an average lifetime of the ferromagnetic state that is preferably smaller than 1 second.

In other embodiments the antiferromagnetic alignment of the two layers can be achieved by an AC field protocol, where the amplitude of the AC field is steadily decreased.

The antiferromagnetic coupling of the two ferromagnetic layers that arises from stray fields of one of the ferromagnetic layers acting on the magnetization of the other ferromagnetic layer, increases if the particle diameter is reduced. The switching field $H_{AF \to F}$ then may become unfavorably large such that the frequency of an oscillatory field must become unfavorably small such that the product of the field and the frequency remains below the biological discomfort level.

Preferred frequencies of oscillating magnetic fields in order to drive the particles through their easy axis hysteresis loop are between 10 kHz and 500 kHz, more preferably between 80 kHz and 300 kHz.

It has been found that frequencies in this range are favorable in combination with the preferred magnetic field strengths that are used for ferromagnetic alignment of the particles and for driving the particles through their easy axis hysteresis loop, in particular to stay below a biological discomfort level. In addition, oscillation frequencies in the given range allow the particles to be magnetized up to a saturation magnetization and demagnetize or be demagnetized to their antiferromagnetic ground state.

The expression $H \cdot f < 5 \cdot 10^9$ $Am^{-1}s^{-1}$ is known as the biological discomfort level, in particular in hyperthermia applications.

Preferably, magnetic saturation along an easy axis of the particle and driving the particle through its easy axis hysteresis loop is obtained under external magnetic field conditions of $H \cdot f < 5 \cdot 10^9$ $Am^{-1}s^{-1}$ (H times f smaller than $5 \cdot 10^9$ A/m per second), wherein H is the externally applied magnetic field and f is the oscillation frequency of the externally applied magnetic field.

At magnetic field conditions operated at values higher than the biological discomfort level, damage of tissue in the region of the applied magnetic field arising from excessive eddy current heating may occur. While the value of the biological discomfort level remains somewhat arbitrary, it is generally agreed upon that it should not be exceeded for prolonged periods of time. It has been found that with the particles of the present invention sufficient heat for hyperthermia application may be generated and that heat generation is even improved compared to existing particles for hyperthermia applications—while staying at operation conditions below the biological discomfort level.

When the particle according to the present invention is subject to magnetic field conditions as described herein, preferably, a temperature increase in a tumor is between 5 Kelvin and 20 Kelvin, preferably between 10 Kelvin and 20 Kelvin, preferably more than 10 Kelvin. Such temperature increase is preferably also available in small tumors having a diameter, for example, as small as 0.5 mm to 2 mm. A temperature increase usually refers to a base reference temperature corresponding to a human body temperature of about 36.5 degree Celsius.

A problem in presently existing magnetic nanoparticles for hyperthermia applications is that they have an insufficient specific heating power in Watts per gramm. Obtaining sufficient temperature increase of a small tumor with a reasonable particle concentration then becomes challenging. A given amount of particles introduced into a tumor may heat the tumor while the tumor is at the same time cooled by surrounding tissue. Small tumors having high surface areas are more efficiently cooled by the surrounding tissue than large tumors having lower surface areas compared to their volume. Thus, only particles having high hysteresis losses, such as the particles of the present invention, will be able to heat up a small tumor to a desired temperature increase of at least 5 Kelvin or more. Due to the efficient heating of the particles of the present invention, preferably smaller concentrations of particles may be introduced into a tumor or other tissue to be treated. Typical amounts of particles to be introduced into a tumor are preferably lower than 100 mg/cm$^3$, preferably as low as 1 mg/cm$^3$ to 10 mg/cm$^3$. Low amounts of particles may be advantageous as the transport of large amounts of particles to a site to be treated and the introduction of the particles into the tissue to be treated may technically not be feasible. Large amounts of particles may be undesirable. For example, high concentration of particles for hyperthermia treatment may have a certain toxicity for living tissue. As such, these particles should preferably not remain in living tissue after treatment or only in doses as low as possible.

For an applied field smaller than the switching field $H_{AF \to F}$ required to switch from the antiferromagnetic to the ferromagnetic alignment, synthetic antiferromagnet particles suspended in a liquid are known to rotate such that their easy magnetization axis aligns perpendicular to the magnetic field. The magnetization directions of both ferromagnetic layers then rotate towards the field axis with the angle between the two magnetization directions decreasing to zero for a sufficiently high applied field.

For hyperthermia hysteresis losses are required. The synthetic antiferromagnet particle must thus be rotated such that its easy axis is aligned with the oscillatory field.

To achieve this, a magnetic alignment field $H_a$ that is larger than the switching field $H_{AF \to F}$ is applied preferably for a time period $\Delta t_a$ longer than the Brown relaxation time $\tau_B$. The Brown relaxation time $\tau_B$ is the rotation time of the particles in the liquid given by thermodynamics.

The synthetic antiferromagnet particles can then align their easy magnetization axis parallel to the applied field and thereby maximize their magnetization parallel to the field and thus minimize the Zeeman energy. Once particles have aligned their easy axes to the field direction, an oscillatory field $H_{osc}$ with an amplitude $H_{osc} > H_{AF \to F}$ is applied preferably with the smallest possible field amplitude required to switch the magnetic moments of the majority of the particles, and a preferably large oscillation frequency, f, but sufficiently small such that the biological discomfort level is not surpassed. The oscillatory field is preferably applied over the longest possible time before the particle's easy axis alignment with the field axis is lost.

Preferably, a sequence comprising an alignment field $H_a$ applied over a time period $\Delta t_a$ such that a good alignment, e.g. $M > 0.8 M_s$, of the particle's easy magnetization axes of the particles along the field $H_a$ is obtained, and an oscillatory field with amplitude $H_{osc} > H_{AF \to F}$ and frequency $f_{osc}$ is applied during the time period $\Delta t_{osc}$ to drive the particles $N = \Delta t_{osc} \cdot f_{osc}$ times through the easy axis hysteresis loop for heat generation.

Alternatively, two non-collinear field directions can be used. In this situation a field can be applied to align the particles, which is smaller than the saturation field. Hence, the easy axes of the particles will rotate about 90° with respect to the alignment field direction. The oscillatory field is then applied in the plane of the layer parallel to a second non-collinear direction with respect to the alignment field. In some embodiments the angle between the alignment field and the oscillatory field can be 90°. In other embodiments, after the alignment field has been applied, a rotating field is applied, where the rotation axis of the rotating field is parallel to the alignment field.

Preferably, in the synthetic antiferromagnet disk-shaped particle, any one of the first or second ferromagnetic layer comprises Fe, Co, Ni, in particular alloy comprising Fe, Co or Ni. Preferably, any one of the first or second ferromagnetic layer comprises FeB, CoB, or a CoFeB alloy. Preferably, any one of the first or second ferromagnetic layer is made of Fe, Co, or a Fe alloy, Co alloy, Ni alloy, in particular a CoFe alloy. Preferably, both the first and the second ferromagnetic layer comprises or is made of Fe, Co, Ni, Fe alloy, Co alloy or a CoFe alloy.

Layers made of or comprising these materials may have a high magnetization or uniaxial anisotropy, which is a necessary condition for obtaining large hysteretic losses. However, this may depend on the manufacturing of the layers and on additional material alloyed to the ferromagnetic layer.

For example, a first ferromagnetic layer may be deposited onto a specifically structured non-magnetic seed layer, for example, to provide a nanocrystalline and flat growth of the successive first ferromagnetic layer. The seed layer, for example tantalum (Ta), can be deposited with sputter deposition or evaporation under an oblique angle to obtain a uniaxial anisotropy in the plane of the ferromagnetic layer deposited onto the structured seed layer. Larger sputter angles to the substrate normal, larger seed layer thicknesses, and smaller thicknesses of the deposited ferromagnetic layer generally lead to larger anisotropies in the ferromagnetic layer.

Alternatively, or additionally, an effective uniaxial magnetic anisotropy in the plane of the layer can be obtained with an elongated shape of the particle in the plane of the ferromagnetic layer.

Alternatively, or additionally, the uniaxial magnetic anisotropy in a ferromagnetic layer may be obtained by alloying a rare earth element, preferably samarium (Sm) into the ferromagnetic layer. The layer may either be deposited or annealed after deposition in a magnetic field applied in the plane of the ferromagnetic layer. Preferably, an amount of a rare earth element is smaller than 25 percent of the ferromagnetic layer, for example 2 percent to 20 percent or 5 percent to 15 percent of the ferromagnetic layer. The percentage refers to atomic percent of the mentioned materials.

Uniaxial magnetic anisotropy may be obtained or enhanced by application of a magnetic field during the deposition or during an annealing process after the deposition.

Preferably, a CoFe alloy is alloyed with a rare earth element, in particular samarium, in the first or in the second ferromagnetic layer or in the first and in the second ferromagnetic layer.

Preferably, in the synthetic antiferromagnet disk-shaped particle, any one of the first or second ferromagnetic layer comprises a rare earth element, in particular samarium.

Preferably, the first and second ferromagnetic layer comprises a rare earth element, in particular samarium.

Preferably, in the synthetic antiferromagnet disk-shaped particle, the first or the second ferromagnetic layer comprises an amorphous, nanocrystalline or polycrystalline samarium alloy, for example CoSm, FeSm, CoSmB, FeSmB or CoFeSmCo.

Preferably, the first and the second ferromagnetic layer comprise an amorphous, nanocrystalline or polycrystalline samarium alloy, for example CoSm, FeSm, CoSmB, FeSmB or CoFeSmCo.

Preferably, in the synthetic antiferromagnet disk-shaped particle, the first and the second ferromagnetic layers are made of a same material.

In the synthetic antiferromagnet disk-shaped particle, at least one of the first or the second ferromagnetic layer may be in a magnetic monodomain state. The first and the second ferromagnetic layer may be in a magnetic monodomain state.

A layer in the synthetic antiferromagnet particle may be a single layer or a multilayer. The first or second ferromagnetic layer may each be a ferromagnetic single layer or a ferromagnetic multi-layer. The interlayer may be a single interlayer or a multi-layer interlayer. Ferromagnetic materials of the layers of a multi-layer may be identical or different. All layers of a ferromagnetic multi-layer are ferromagnetic layers. Non-magnetic materials of the layers of a multi-layer interlayer may be identical or may be different. All multi-layers of an interlayer are non-magnetic layers.

Preferably, the synthetic antiferromagnet disk-shaped particle according to the invention has a circular or elliptic circumference.

The synthetic antiferromagnet disk-shaped particle may also have a rectangular or square perimeter with sharp or rounded edges.

The shape and size of the perimeter of the synthetic antiferromagnet disk-shaped particle may be selected to influence the anisotropy of the synthetic antiferromagnet particle (shape anisotropy). In some embodiments the required anisotropy is realized by an effective anisotropy, where due to elongated shapes of the particles a shape anisotropy occurs which leads to an effective anisotropy.

A dimension of the synthetic antiferromagnet disk-shaped particle, preferably a diameter of the particle, may, for example, be between 10 nanometer and 5000 nanometer, preferably between 20 nanometer and 2500 nanometer, more preferably between 40 nanometer and 1000 nanometer, for example 50 nanometer, 80 nanometer, 120 nanometer, 250 nanometer, 500 nanometer.

A thickness of the synthetic antiferromagnet disk-shaped particle may, for example, be between 5 nanometer and 1000 nanometer, preferably between 10 nanometer and 500 nanometer, more preferably between 10 nanometer and 200 nanometer.

A thickness of at least the first or the second ferromagnetic layer may, for example, be between 1 nanometer and 500 nanometer, preferably between 2 nanometer and 200 nanometer, more preferably between 4 nanometer and 50 nanometer, for example 6 nanometer, 10 nanometer, 25 nanometer.

A thickness of the interlayer may, for example, be between 0.5 nanometer and 200 nanometer, preferably between 1 nanometer and 80 nanometer, more preferably, between 1 nanometer and 20 nanometer, for example 2 nanometer, 4 nanometer, 6 nanometer.

The magnetic characteristics of the synthetic antiferromagnet particle, specifically, the switching fields $H_{AF \rightarrow F}$ and $H_{F \rightarrow AF}$ may be influenced and optimized by a specific selection of particle dimensions, particle shape, an extent of uniaxial anisotropy of the ferromagnetic layers, thicknesses and magnetizations of the ferromagnetic layers, the interlayer thickness and in some embodiments of the synthetic antiferromagnet particle also by a ferromagnetic Ruderman-Kittel-Kasuya-Yosida (RKKY) interaction through the interlayer.

In some embodiments of the synthetic antiferromagnet particle, the material of the interlayer can be chosen to exhibit a ferromagnetic RKKY exchange interaction to partially compensate the antiferromagnetic alignment arising from the stray field of the ferromagnetic layers.

A type of ferromagnetic or antiferromagnetic alignment that can exist between two magnetic materials separated by a non-magnetic spacer layer is known as RKKY coupling. Generally, in synthetic antiferromagnet particles, for example as described in US2008/0206891, the antiferromagnetic coupling between the two ferromagnetic layers is enhanced based on RKKY coupling through, for example, a ruthenium (Ru) spacer layer of 0.8 nm thickness.

In other embodiments the adjacent ferromagnetic layers are not exchange coupled.

In the present invention, the antiferromagnetic coupling arising from the stray fields of the ferromagnetic layers can be very strong for particles with smaller diameters, such that a ferromagnetic orientation of the ferromagnetic layers can only be achieved when a large external magnetic field $H_{AF \rightarrow F}$ is applied. The antiferromagnetic coupling arising from the interaction of the stray field from one ferromagnetic layer with the magnetization of the other ferromagnetic layer, can then be weakened by ferromagnetic RKKY coupling through the interlayer. By this, a ferromagnetically aligned state of the two ferromagnetic layers in the particle and undergoing a hysteresis loop for heat generation may be achieved while keeping the magnetic field conditions below the biological discomfort level.

In some embodiments of the antiferromagnetic disk-shaped particle according to the invention, the interlayer promotes a RKKY coupling between the first and the second ferromagnetic layer, thereby weakening the antiferromagnetic coupling between the first and the second ferromagnetic layer, which antiferromagnetic coupling is caused by magnetic stray fields of the first and the second ferromagnetic layers. Such a ferromagnetic RKKY interaction can also be used to lower the energy barrier between the ferromagnetically and antiferromagnetically aligned states, such that the product of this energy barrier and layer volume becomes smaller than 25 $k_B T$, preferably smaller 10 $k_B T$ or even smaller than 5 $k_B T$ at zero external field. This leads to an average lifetime of the ferromagnetic state that is preferably smaller than 1 second.

Various non-magnetic materials are suitable for an interlayer, either promoting or non-promoting a RKKY coupling. If no RKKY coupling is promoted, then the antiferromagnetic coupling of the first and second ferromagnetic layers bases in the interaction of their stray fields only.

Materials for interlayers are, for example, ruthenium (Ru), tantalum (Ta), titanium (Ti), copper (Cu), gold (Au), iridium (Ir) or platinum (Pt).

A preferred material for an interlayer promoting a ferromagnetic RKKY coupling is platinum (Pt) or iridium (Ir) (thus weakening the antiferromagnetic coupling between the two ferromagnetic layers)). In the case of Pt the ferromagnetic RKKY interaction can be adjusted with the Pt layer thickness that is preferably between 1 nm and 4 nm. In case of Ir a selection of the layer thicknesses between 0.5 nm and 2 nm leads to an RKKY coupling that oscillates between antiferromagnetic and ferromagnetic with an amplitude decaying with increasing interlayer thickness.

Interlayers comprising or being made of platinum or of iridium preferably have a thickness between 0.5 nm and 4 nm, more preferably between 0.7 nm and 3 nm, for example about 1.3 nm.

It has been found that in some particle configuration a strong antiferromagnetic coupling of the two ferromagnetic layers may be lowered by an appropriate choice of a platinum containing interlayer. Preferably, a platinum alloy, preferably comprising iridium (Ir) is used for the interlayer.

Preferably, the interlayer comprises or is made of a PtIr alloy, for example $Pt_{1-x}Ir_x$ alloy, preferably to obtain an adjustable ferromagnetic RKKY interaction between the first and second ferromagnetic layer to partially compensate the antiferromagnet interaction arising from the stray fields of the ferromagnetic layers. It has been found that the RKKY coupling between the first and the second ferromagnetic layer is lower for higher concentrations of iridium in the interlayer or larger thicknesses of the interlayer. Depending on the desired strength of the antiferromagnetic coupling between the first and the second ferromagnetic layer, the amount of iridium in the alloy of the interlayer is enhanced or lowered.

Manufacturing methods for synthetic antiferromagnet disk-shaped particles are various, including, for example, the methods as described in US2008/0206891. The layers of the particles may be manufactured, for example, by layer-by-layer material deposition, for example sputter-deposition. Sputter-deposition may, for example, occur under an oblique angle with reference to the plane of the layer to be deposited. Alternatively, sputter-deposition may be used, for example, to deposit a seed layer, which then may lead to a uniaxial anisotropy of the successive ferromagnetic layer deposited onto the seed layer. Material deposition may occur in an applied magnetic field. Preferably, a uniaxial magnetic field is applied to align the magnetic moments of a ferromagnetic material during deposition to induce a uniaxial anisotropy in the ferromagnetic layer. Such an induced magnetic anisotropy can become particularly large for Co-alloys containing for example Sm.

Fields of application of antiferromagnet particles as described herein are various. While the particles of the present invention are particularly suited for hyperthermia applications, their use is not limited to such applications. In particular the use of the antiferromagnet particles is suitable for therapeutic as well as for non-therapeutic applications.

According to an aspect, the invention relates to non-therapeutic use of synthetic antiferromagnet disk-shaped particles as described in the application.

The non-therapeutic use of the antiferromagnet disk-shaped particles may relate to one or several of the application fields mentioned in the following.

The particles may be used in various fields, in particular in biology and medicine. The following application fields are mentioned by way of example: magnetically based filtering and separation methods, biomolecule purification and cell separation, magnetic particle imaging, temperature-induced drug release, temperature-induced triggering of chemical reactions, particles used as contrast agents in MRI (magnetic resonance imaging), MPI (magnetic particle imaging), biomagnetic sensing, multiplex magnetic labeling.

For filtering purposes, the particles may, for example, be chemically or biochemically functionalized to preferentially bind to a molecular or biological entity present in a liquid, for example a body liquid. A magnetic field sufficiently strong to magnetize the particles will then drive the particles into a saturated state. A magnetic field gradient then allows extracting the particles from the liquid.

Drug release from a suitably functionalized particle shell can, for example, be triggered by the heat from the magnetization losses of the particle.

Heat provided for chemical reactions, may, for example, be used for hardening of glue or for the polymerization of polymer materials.

The particles may be used as such or may be specifically prepared for their intended use. The particles, may, for example comprise oxidation protection of the magnetic layers, may comprise surface functionalization, for example, to obtain colloidal stability or to obtain a desired biocompatibility. The particles may include other biomedical functions such as biological specifity, for example, to attach to tumor-specific cells or to prevent an uptake of the particles by macrophages. The particles may also contain drugs or chemical substances that can be released when the particle is heated or may contain chemical substances that undergo a heat-driven reaction. The particles may also comprise a sacrificial layer used in the manufacturing process of the particles. This sacrificial layer may be removed before use of the particle or may remain if no unintentional or undesirable effect on the intended use of the particle is present or to be expected. Typically, a sacrificial layer is used to separate a particle structure microfabricated on a substrate to remove said particle structure from the substrate, for example from a wafer.

The synthetic antiferromagnet disk-shaped particle may comprise at least a further layer, preferably a seed layer or an outer layer, capable to perform at least one of the following: oxidation protection of the first and the second ferromagnetic layer; colloidal stability of the particle; biomedical function such as for example attachment capability to specific cells, in particular to tumor-specific cells; prevention of uptake of the particle by macrophages; release or reaction of a chemical substance comprised in the particle, for example a drug, upon heating of the particle. The particle may contain a drug or chemical substances that can be released when the particle is heated or the particle may contain chemical substances that undergo a heat-driven reaction.

A further layer may in particular be a seed layer used in manufacturing of the particle, in particular to influence the magnetic properties of the first ferromagnetic layer. The seed layer may comprise an additional function, such as for example oxidation protection of the neighboring ferromagnetic layer or improvement of colloidal stability of the particle.

A further layer may enclose the particle. A further layer may be arranged next to the first or to the second ferromagnetic layer or may be arranged next to both the first and to the second ferromagnetic layer. A further layer may be applied to the first or to the second ferromagnetic layer. A further layer may be applied to both, the first and the second ferromagnetic layer. The particle may comprise one or several further layers comprising any one or a combination of the above-mentioned functions.

For manufacturing a synthetic antiferromagnet particle, preferably, the first ferromagnetic layer, the interlayer and the second ferromagnetic layer are subsequently deposited onto a suitable non-magnetic seed layer. The seed layer is preferably provided on a sacrificial layer on a flat substrate, preferably a silicon or glass wafer.

Other layers can be added between the sacrificial layer and the seed layer or onto a second or top ferromagnetic layer for oxidation protection or to facilitate chemical or biochemical functionalization, specifically the bonding of molecules to these layers of the particle.

All layers are preferably deposited by a vacuum-based deposition process, preferably plasma deposition or evaporation. The planar geometry of the synthetic antiferromagnet particle is defined by the fabrication process. The thicknesses of the layers of the synthetic antiferromagnet particle are defined by a deposition rate time. The synthetic antiferromagnet particle can be removed from its substrate, such as for example from a wafer, for example by a dissolution or etching of the sacrificial layer. By such a process a seed layer may remain on the particle.

According to the invention, there is also provided a suspension for hyperthermia application comprising a plurality of synthetic antiferromagnet particles according to the present invention and as described herein and a solvent.

The invention also relates to a method for magnetic hyperthermia. In particular, the invention relates to a method for magnetically heating an antiferromagnet disk-shaped particle according to the invention and as described herein, wherein the method is for therapeutic applications such as for example magnetic hyperthermia, as well as for non-therapeutic applications, such as for example temperature-induced chemical reactions. In particular the method relates to magnetic hyperthermia using synthetic antiferromagnet particles, more particularly the synthetic antiferromagnet particles according to the present invention. The method also relates to a method for magnetically heating magnetic particles, preferably mechanically heating antiferromagnet particles, more preferably synthetic antiferromagnet particles according to the present invention.

The method comprises application of a time varying magnetic field to interact with magnetic particles, the magnetic particles comprising a magnetic easy axis, wherein a field protocol is repeated. The field protocol comprises applying an alignment field in a first direction with a field amplitude $H_a$, which field amplitude $H_a$ is sufficiently large to saturate the magnetic particles, and with an application duration $\Delta t_a$, which application duration $\Delta t_a$ is sufficiently long to rotate the magnetic easy axis of the magnetic particles into the first direction. The field protocol further comprises applying an oscillatory field with the field amplitude $H_{osc}$ and a frequency f, so that the inverse of the frequency 1/f is smaller than $\Delta t_a$.

A field axis of the alignment field may be collinear or non-collinear to a field axis of the oscillatory field. The field amplitude $H_a$ and the field amplitude $H_{osc}$, may be equally large or may be different.

Details of the method for magnetic hyperthermia as well as details of the method for heating magnetic particles for therapeutic as well as non-therapeutic use have been described above relating to the synthetic antiferromagnet disk-shaped particle and will not be repeated.

Preferably, the method for magnetically heating magnetic particles for therapeutic and for non-therapeutic use, in particular for magnetic hyperthermia using magnetic particles, and in particular for magnetically heating the antiferromagnet disk-shaped particle of the present invention, comprises providing a magnetic field between 10 Millitesla and 140 Millitesla and using an oscillation frequency of the magnetic field between 10 kHz and 500 kHz.

A 'disk-shaped' particle is herein understood as a particle having substantially flat and parallel upper and lower sides. Parallelism and flatness of the upper and lower sides includes exact values but may also deviate from exact values. For example, in very small particles having small lateral dimensions, e.g. a small diameter, the relative arrangement of the upper and lower sides of the particle generally deviates from an exact parallelism and flatness of the upper and lower sides.

Preferably, a disk-shaped particle has a height dimension (thickness) of the particle that is smaller than a lateral dimension of the particle. A perimeter of a particle may be a circumference and may be circular or elliptical. A perimeter of a disk-shaped particle may also have the shape of a rectangle, triangle or a polygon.

If not otherwise mentioned, a temperature refers to room temperature. Temperature increases of tissue, in particular with reference to hyperthermia applications, refer to a reference temperature corresponding to an elevated body temperature of typically about 36.5 degree Celsius in humans.

A 'uniaxial magnetic anisotropy in the plane of the ferromagnetic layer' of the particle is understood as a magnetic anisotropy in the plane of each of the ferromagnetic layers along one specific spatial axis in the plane of the particle. A given value of the anisotropy refers to the magnetic anisotropy in the plane of one ferromagnetic layer. In case of a ferromagnetic layer being formed of a multi-layer, the anisotropy refers to the anisotropy of the ensemble of the multi-layer.

For a heterogeneous mixture of a plurality of synthetic antiferromagnet disk-shaped particles and a solvent, in particular a liquid, the term 'suspension' is used in the application for all size ranges of the particles defined in the application. Thus, the term 'suspension' also includes 'dispersion', which term is more commonly used for particles in liquids, where a particle size is below 1 micrometer.

The invention also relates to a system for magnetically heating magnetic particles. The system comprises a plurality of synthetic antiferromagnet disk-shaped particles as described in the application and an apparatus for magnetically heating the synthetic antiferromagnet disk-shaped particles. The apparatus comprises a magnetic field generator and a processor, wherein the magnetic field generator is adapted to and the processor is programmed to perform the method as described in the application. Preferably, the system is for hyperthermia applications.

The invention is further described with regard to examples, which are illustrated by means of the following drawings, wherein.

Figures 4, 5:
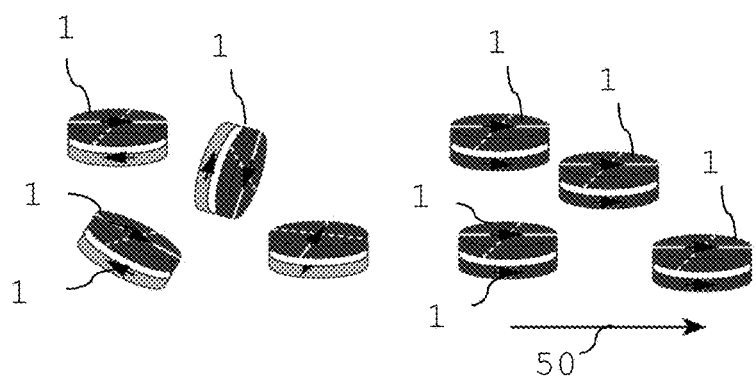
Figure 6:
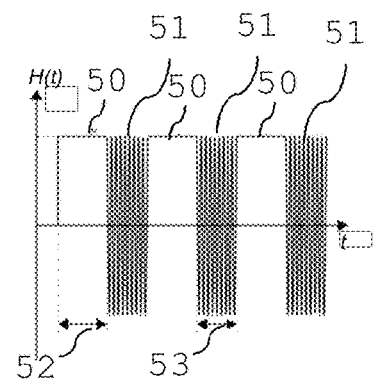
Figure 7:
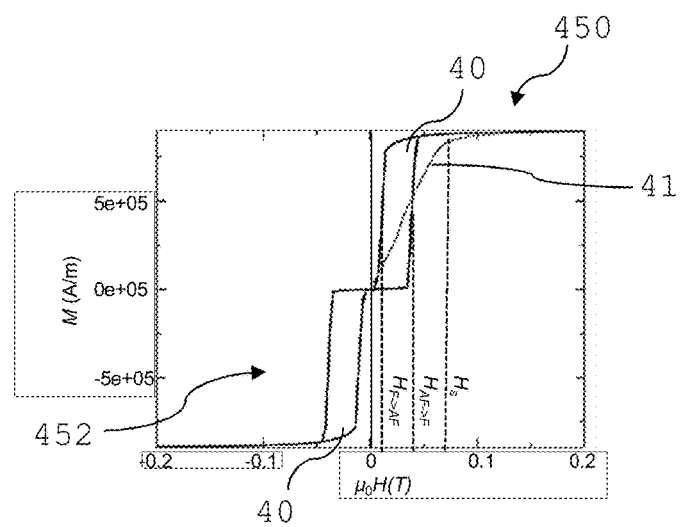
Figure 8:
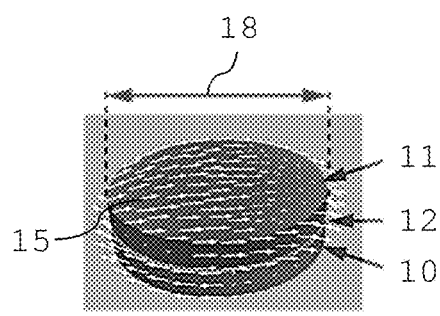
Figure 9:
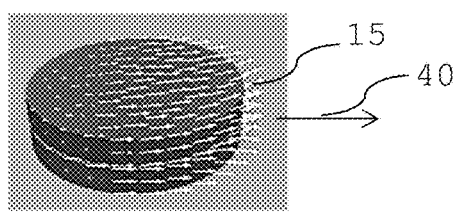
Figure 10:
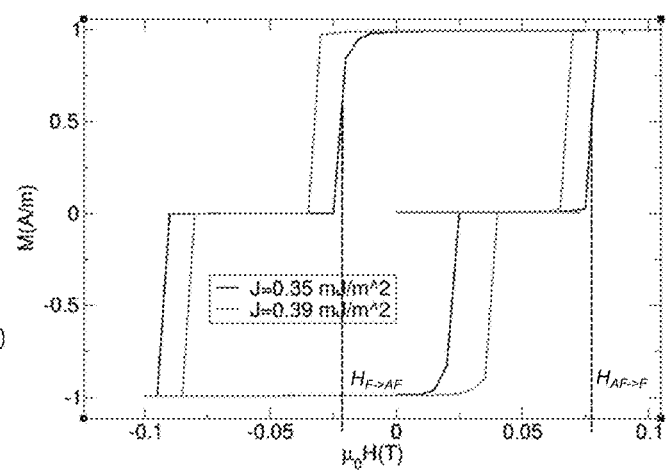
Figure 11:
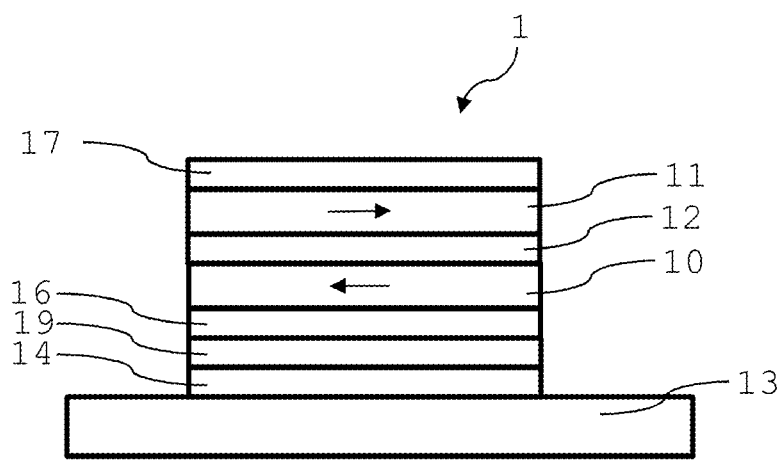
Figure 12:
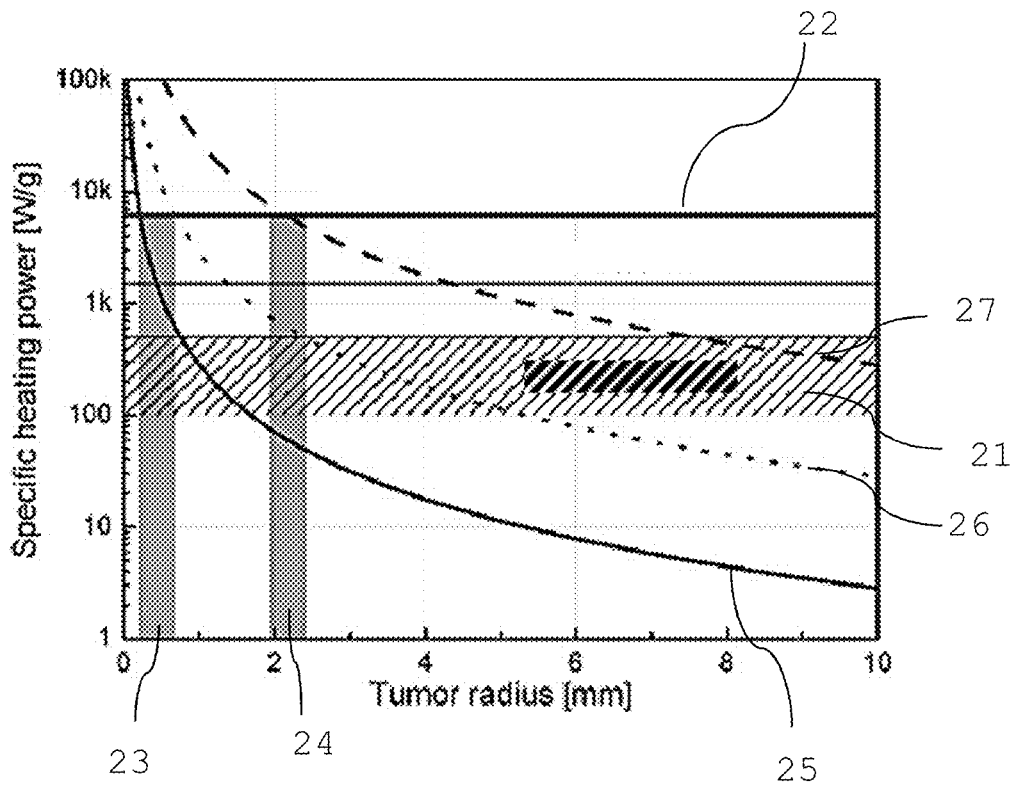

FIGS. 4-6 shows an operation mode of synthetic antiferromagnet particles in externally applied magnetic field (FIG. 4: random alignment; FIG. 5: alignment of the easy axis; FIG. 6: magnetic field sequence);

FIG. 7 shows easy and hard axis hysteresis loops of a micropatterned disk-shaped antiferromagnet particle;

FIG. 8-10 are illustrations of a synthetic antiferromagnet particle with ferromagnetic RKKY exchange between ferromagnetic layers and its hysteresis loop;

FIG. 11 is a schematic layer structure of a functionalized synthetic antiferromagnet particle;

FIG. 12 is an illustration of particle's specific heat loss in tumors.

Figure 1:
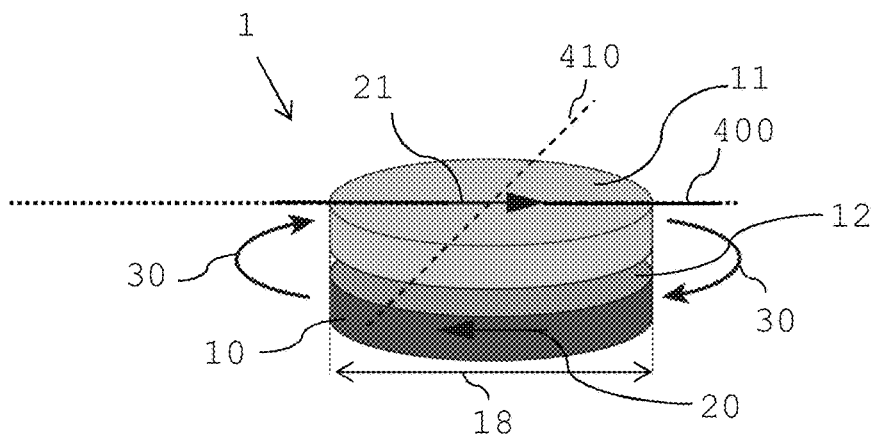
FIG. 1 shows a synthetic antiferromagnet disk-shaped particle.

FIG. 1 illustrates a synthetic antiferromagnet particle 1. The particle 1 has a circular diameter and is disk-shaped. A first ferromagnetic layer 10 and a second ferromagnetic layer 11 are arranged above each other, separated by a non-magnetic interlayer 12.

Arrows 20, 21 indicate the orientation of the magnetic moments of the first and the second ferromagnetic layers 10, 11 according to their uniaxial anisotropy $K_u$ in the plane of the ferromagnetic layers 10, 11. The arrows 20, 21 directing in opposite directions also indicate the antiferromagnetic alignment of the magnetic moments of the first and the second ferromagnetic layers 10, 11. The antiferromagnetic coupling may be obtained by the magnetic stray field of the first and second layers, which stray field is indicated by arrows 30.

Dotted line 400 indicates the easy magnetization axis of both ferromagnetic layers 10, 11 of the particle 1. The magnetization is arranged in the planes of the ferromagnetic layers 10, 11. Dashed line 410 indicates the hard magnetization axis of both ferromagnetic layers 10, 11 of the particle 1. The hard magnetization axis is arranged perpendicular to the easy magnetization axis.

The diameter 18 of the particle 1 may, for example, be about 500 nm. The height of the particle 1 may, for example, be about 14 nm. Thereby, the thicknesses of the first and second ferromagnetic layer 10, 11 may be about 6 nm and the thickness of the interlayer 12 may be about 2 nm.

The first and second ferromagnetic layer 10, 11 are preferably made of Co, Fe, CoFe-alloy, FeB-alloy, CoB-alloy or FeCoB-alloy, possibly comprising, for example Ni. Preferably, the first and second ferromagnetic layers 10, 11 are CoFeB layers having a uniaxial anisotropy in the plane of each ferromagnetic layers of 20 kJ/m$^3$ and a saturation magnetization of M$_s$>1200 kA/m.

The material of the interlayer preferably is Ta.

Figures 2, 3:
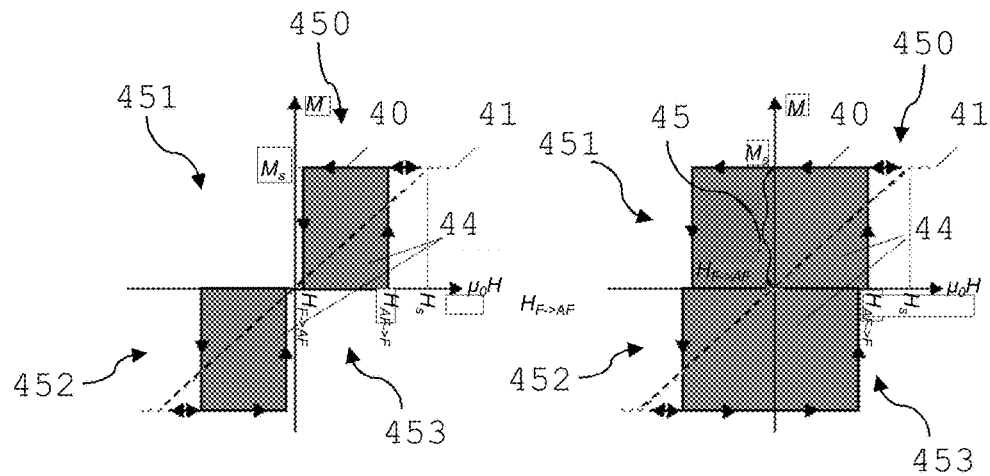
FIG. 2 illustrates an idealized view of the easy axis and hard axis hysteresis loops for magnetic fields applied in the plane of the ferromagnetic layer of a synthetic antiferromagnet particle.
FIG. 3 illustrates an idealized view of the easy axis and hard axis hysteresis loops for magnetic fields applied in the plane of the ferromagnetic layer of another synthetic antiferromagnet particle.

In the M(H)-coordinate system shown in FIG. 2 the magnetization 14 of the particle dependent on the externally applied magnetic field H is depicted. The solid black line 40 illustrates an ideal easy-axis hysteresis loop in the plane of the ferromagnetic layers to obtain largest magnetization losses and an antiferromagnetic ground state of the particle with vanishing magnetic moment at zero magnetic field. The areas 44 circumscribed by the hysteresis loop 40 are representative for the hysteresis losses in the particle 1, for example as shown in FIG. 1. The hysteresis loops in the first 450 and in the third 452 quadrant of the M(H)-coordinate system have an exact rectangular shape for an idealized antiferromagnet particle.

When the externally applied magnetic field reaches the saturation field H$_s$ of the ferromagnetic layer, the magnetic moments in the ferromagnetic layer are oriented into the direction of the magnetic field and the saturation magnetization M$_s$ is reached.

In the first quadrant 450 of the M(H)-coordinate system the hysteresis loop for positive magnetic fields and positive magnetization values is shown. In the third quadrant 452 of the M(H)-coordinate system the hysteresis loop for negative magnetic fields and negative magnetization values is shown. For negative fields, the same magnetization process occurs for the other ferromagnetic layer such that a hysteresis loop occurs for the equivalent negative fields, and negative magnetization values.

At zero magnetic field the particle represented in FIG. 2 is in its antiparallel configuration: the magnetic moments of the first and the second ferromagnetic layer 10, 11 are oriented in an antiparallel manner, for example as shown in FIG. 1. The particle has a vanishing total magnetization. The magnetization orientation characteristic for a synthetic antiferromagnet particle is re-established when the magnetic field is zero.

In real particles, preferably, the saturation magnetization is substantially reached and the hysteresis loops have a substantially rectangular shape. Thus, preferably, for a field H>H$_{AF \to F}$>0 applied along the uniaxial anisotropy axis in the plane of the ferromagnetic layers, the alignment of the magnetizations of the first and the second ferromagnetic layer 10, 11 is substantially parallel, for example larger than 80 percent of the saturation magnetization (0.8·M$_s$). Preferably, the magnetization is even larger than 90 percent of the saturation magnetization (0.9·M$_s$).

In the antiferromagnet disk-shaped particle according to the present invention, a hard axis magnetic saturation field of the particle is larger than an easy axis magnetic saturation field of the particle.

The saturation field H$_s$ is the field required to align the magnetization of the ferromagnetic layers parallel to a field applied in the plane of the layer, perpendicular to the uniaxial anisotropy axis (hard axis magnetization process) This magnetization process is illustrated by the dashed line 41, showing no hysteresis losses.

The particles of the present invention have ferromagnetic layers with a significant uniaxial anisotropy in the plane of the ferromagnetic layers.

For a field aligned along this uniaxial anisotropy axis the ferromagnetic layer with a magnetization opposite to the direction of the applied field switches at a switching field H$_{AF \to F}$ (0<H$_{AF \to F}$<H$_s$ and reaches a preferred magnetization M>0.9·M$_s$ within a small field interval ΔH«H$_{AF \to F}$ when the field is increased. For a decreasing field the magnetization of the ferromagnetic layer remains close to the saturation value, preferably at M>0.8·M$_s$ and switches back to antiferromagnetic alignment abruptly at a field H$_{F \to AF}$>0, which field is close to 0, within a field interval ΔH<H$_{F \to AF}$, such that the area of the partial hysteresis loop is maximized.

FIG. 3 illustrates idealized hysteresis loops of a synthetic antiferromagnet particle with even higher magnetization loss, showing remanence at zero field.

The same reference numbers are used for the same or similar elements.

The hysteresis loops extend over all four quadrants 450, 451, 452, 453 of the M(H)-coordinate system.

The particle and its hysteresis loop is designed such that the antiferromagnetic coupling of the first and second antiferromagnetic layer 10, 11 is too weak to return the particle into its antiferromagnetic ground state when the external magnetic field H is turned to zero.

The particle shown in the example of FIG. 3 is also designed that thermal decay into the ferromagnetic ground state occurs as shown by arrow 45. Thermal decay occurs at room temperature or body temperature in a time preferably below 10 seconds.

Alternatively, an oscillatory magnetic field with a decaying field magnitude may be applied to the particle to return the particle into the antiferromagnetic ground state.

For hyperthermia applications or also other applications, where the synthetic antiferromagnet particle is heated through hysteretic losses, preferably, a sequence of a magnetic alignment field and a magnetic oscillatory field is applied to the particle.

This is outlined in more detail in FIGS. 4, 5 and 6.

In suspensions comprising a plurality of synthetic antiferromagnet particles, for example as shown in FIG. 1, no preferential particle orientation exists in the absence of an external magnetic field (FIG. 4). The particles in a liquid have a random orientation and rotate with a characteristic time TB, the Brownian relaxation time.

In order to obtain the highest magnetic losses when applying oscillatory magnetic fields, the particles must be forced to align their easy magnetization axis with the uniaxial direction of the applied external field. Such an alignment is achieved by application of a magnetic field with a magnitude larger than the easy axis saturation field but smaller than the hard axis saturation field over a time duration $\Delta t_a$ longer than the Brown relaxation time of the particles.

Thus, if an alignment field $H_a$ with $H_{AF \to F} < H_a < H_s$ is applied for a time duration 52 of $\Delta t_a > \tau_B$, the easy-axes of all particles align with the field (FIG. 5).

Subsequently, an oscillatory field $H_{osc}$ with a magnitude larger than $H_{AF \to F}$ to drive the magnetization of the particles through their easy-axis hysteresis loop is applied, preferably over a time duration 53 of $\Delta t_{osc}$ shorter than the Brown relaxation time of the particles.

Afterwards, the particles are re-aligned again before the oscillatory field is again applied.

In FIG. 6 the magnetic field sequence is shown that is required to align the particles with their easy axis and subsequently experience their easy axis hysteresis loops in the layer plane by the applied oscillatory field.

The alignment field is applied to the particle 1 to achieve an alignment of, for example $M > 0.8 M_s$, of the particle's easy magnetization axes along the alignment field. The oscillatory field with amplitude $H_{osc}$ and frequency $f_{osc}$ is applied during the time period $\Delta t_{osc}$ to drive the particles $N = \Delta t_{osc} \cdot f_{osc}$ times through the easy axis hysteresis loop for heat generation before the particle returns to the antiferromagnetic ground state or is made to return to the antiferromagnetic ground state.

FIG. 4 shows the status of the particles in the suspension before application of a magnetic field and after the particles have gained their random orientation and antiferromagnetic ground state after magnetic field application, e.g. after hyperthermia treatment. Typically, the random orientation of the particles is achieved in 10 ms to 100 ms after the magnetic field has been turned off, while the antiferromagnetic ground state is achieved in less than 10 seconds after the magnetic field has been turned off.

The diameter of the synthetic antiferromagnet disk-shaped particles may be rather large, e.g. 500 nm, compared to superparamagnetic particles (<20 nm) commonly used for hyperthermia applications. Accordingly, the Brownian relaxation time may be rather large until the particles rotate back to an antiparallel ground state and random orientation in a liquid. Accordingly, there is plenty of time to drive the particles several times through their easy axis hysteresis loop in an applied oscillating field.

FIG. 7 shows a hysteretic easy 40 and non-hysteretic hard-axis 41 hysteresis loops of a micropatterned antiferromagnet particle with a diameter of 500 nm. The first and second ferromagnetic layers are 6 nm thick CoFeB films, an amorphous ferromagnetic alloy with a saturation magnetization $\mu_0 M_3 = 1.75$ T, and an exchange stiffness A=15 pJ/m. The first and second ferromagnetic layers are antiferromagnetically coupled and each layer has a uniaxial anisotropy in the plane of the ferromagnetic layer of 20 kJ/m³. The first and second ferromagnetic layers are separated by a 2 nm non-magnetic interlayer, for example tantalum.

The ferromagnetic state of the particle occurs after application of a magnetic field of slightly less than 50 mT along the easy axis. As may be seen in the drawing, the easy axis hysteresis loop has an almost rectangular shape in the first and the third quadrant of the M(H)-coordinate system and comprises slightly rounded edges close to the saturation magnetization.

FIG. 8 and FIG. 9 show a disk-shaped synthetic antiferromagnet particle with a diameter 18 of 50 nm. The particle is shown in the antiferromagnetic ground state (FIG. 8) and in the ferromagnetic state after application of a field larger than $H_{AF \to F}$ (FIG. 9) along the easy uniaxial anisotropy axis in the plane of ferromagnetic layer. The first and second ferromagnetic layers 10, 11 are 6 nm thick amorphous CoFeB films with a saturation magnetization $\mu_0 M_s = 1.75$ T, and an exchange stiffness A=15 Wm, each having a uniaxial anisotropy in the plane of the ferromagnetic layer of 50 kJ/m³. The two ferromagnetic layers are separated by a 2 nm thick interlayer made of a Ft/Ir alloy with a ferromagnetic RKKY exchange of either 0.35 mJ/m² or 0.39 mJ/m², required to obtain a thermal decay of the ferromagnetic state back into the antiferromagnetic ground state in a reasonable short time, e.g. in less than 10s, preferably in about is. The two ferromagnetic layers are antiferromagnetically coupled with a homogeneous antiparallel magnetization 15 along the easy axis (ground state FIG. 8).

The ferromagnetic state is shown in FIG. 9 with the two ferromagnetic layers 10, 11 having a parallel magnetization 15 along the easy axis and in the direction of the applied magnetic field. The ferromagnetic state occurs after application of a field of about 80 mT along the easy axis 40.

In FIG. 10, the easy axis hysteresis loops of the particle of FIG. 8 and FIG. 9 is shown with the interlayer 12 causing a ferromagnetic RKKY interaction $J_{FM}$ required to obtain a thermal decay of the ferromagnetic state back into the antiferromagnetic ground state in a reasonable short time, e.g. less than 10s, preferably in about is. The ferromagnetic RKKY exchange of the interlayer partially compensates the antiferromagnetic coupling arising from the stray field of the two ferromagnetic layers 10, 11.

The hysteresis loops for RKKY interaction for two different strengths of the interaction is shown. The dark line shows the hysteresis loop for the particle having a RKKY interaction of $J_{FM} = 0.35$ mJ/m². The light line shows the hysteresis loop for the particle having a RKKY interaction of $J_{FM} = 0.39$ mJ/m².

At zero field a remanent magnetization nearly equal to the saturation magnetization is observed and the particle remains locked in the ferromagnetic state. The ferromagnetic state is less stable than the antiferromagnetic state and because of the partial compensation of the antiferromagnetic coupling from the stray field by the ferromagnetic RKKY exchange, the energy barrier between the states is sufficiently small to allow a thermal decay to the antiferromagnetic ground state within about 1 s.

FIG. 11 is a schematic illustration of an example of a layered particle structure of a functionalized disk-shaped antiferromagnet particle 1. The particle is manufactured by a layer-wise deposition of different materials on a substrate 13, for example on a wafer, such as a silicon or glass wafer. Directly above the substrate, a sacrificial layer 14 is deposited to allow the particle construction to be removed from the substrate after manufacture of the particle 1. Preferably, a sacrificial layer 14 is a water soluble layer or a layer that can be etched for example in citric acid. For example, the sacrificial layer is a 5 nm thick layer, for example comprising magnesium or copper or MgO. Also other solvents may be used to remove the sacrificial layer 14.

The further layers are—when seen from bottom to top: a first or bottom functionalization layer 19 on top of the sacrificial layer 14, a seed layer 16, a first ferromagnetic layer 10, a non-magnetic interlayer 12, a second ferromagnetic layer 11 and a second or top functionalization layer 17.

The seed layer 16 is, for example, a 2 nm to 6 nm thick layer, for example comprising or being made of Ta. The seed layer 16 is provided to promote an appropriate growth of the first ferromagnetic layer 10 and to obtain specific magnetic properties. Such specific magnetic properties, may, for example, be a sufficiently small or absent perpendicular magnetic anisotropy to keep the magnetization of the ferromagnetic layers 10, 11 in the plane, and an in-plane uniaxial magnetic anisotropy $K_u$, in the ferromagnetic layer plane, to align the magnetization along this direction, to obtain a single-domain state, and to design switching fields $H_{AF \to F}$ and $H_{F \to AF}$ optimized to obtain largest magnetization loss within the boundaries defined by the biological discomfort level for oscillatory fields.

The seed layer 16 may be deposited, for example by sputtering under an oblique angle, to give the seed layer 16 a specific structure. The seed layer 16 may, for example, be a nano-crystalline tantalum layer.

The first ferromagnetic layer 10 grown on or deposited onto such a structured seed layer 16 then shows a uniaxial anisotropy in the plane of the first ferromagnetic layer.

During deposition of the first and of the second ferromagnetic layers 10, 11 a uniaxial magnetic field may be applied. The strength of this applied magnetic field is sufficiently strong to align the magnetic moments during the deposition along the field direction to obtain an induced uniaxial anisotropy in the layer plane in the ferromagnetic layers 10, 11. During the deposition of the second ferromagnetic layer 11, the applied field must be sufficiently strong to align the magnetization of the second ferromagnetic layer 11 during its growth in the presence of the stray field of the first ferromagnetic layer 10.

The first and second ferromagnetic layers 10, 11 are, for example, 6 nm thick, for example comprising an Fe-alloy, Co-alloy or a CoFe alloy, for example CoFeB, CoFe, FeB, CoB.

In order to further increase the magnetic anisotropy induced, for example, by a magnetic field applied during sputtering of the ferromagnetic layers 10, 11, for example a CoFeB layer is alloyed with a rare earth metal, in particular Sm. Amorphous Sm (20%) Co (80%) layer can develop a significant uniaxial anisotropy in the layer plane induced by an applied field during layer growth or by an annealing process in a field following the deposition. An amorphous structure of the ferromagnetic layers arises from the Sm in the Sm(20%)Co(80%) alloy. Thus, the obtainable anisotropy in the plane of the ferromagnetic layers may be tuned by selecting the Sm/B-ratio in the CoFeBSm alloy or also in a Sm/CoFe ratio in an CoFeSm alloy. A uniaxial anisotropy in the layer plane of 50 kJ/m³ may be obtained in amorphous CoSm or CoFeSm or CoFeBSm layers of e.g. 6 nm thickness.

The non-magnetic interlayer 12 may have a thickness of e.g. 2 nm and is made, for example, of Ta, $Ta_{1-x}Pt_x$, $Ir_{1-x}Pt_x$.

The bottom functionalization layer 19 and the top functionalization layer 17 may protect the particle layer construction, from for example oxidation. More particularly, the two functionalization layers 17, 19 are layers permitting a biological, biomedical, physical or chemical functionalization of the particle, i.e. the binding of specific molecules to these layers, for example to obtain colloidal stability of the particle in liquids, to provide attachment capability of the particle to specific cells, to prevent uptake of the particle by macrophages, to enable release or reaction of a chemical substance comprised in the particle, for example a drug, upon heating of the particle. Functionalization layers may have a thickness of, for example, 2 nm to 10 nm. Materials for functionalization layers are, for example, Au, C, Ti-oxide, Ta, Si-oxide. The bottom and the top functionalization layer 17, 19 may be identical or may be different. The bottom and the top functionalization layer 17, 19 may be designed and chosen depending on the desired function of the synthetic antiferromagnet particle.

A chemical or biochemical functionalization is preferably obtained after dissolution of the particle from the wafer by adding specific molecules to the functionalization layers 17 or 19 that are comprised of materials to obtain a suitable bonding to the molecules.

FIG. 12 illustrates the specific heating power required to obtain a temperature rise of 15 K within a tumor of a given radius. The curved lines 25, 26, 27 show the requirements for the particle's specific heat loss. Solid line 25 represents a particle concentration of 100 mg/cm³, dotted line 26 represents a particle concentration of 10 mg/cm³ and dashed line 27 represents a particle concentration of 1 mg/cm³.

The typical specific power losses (SLP) for typical superparamagnetic particles (MNP) is indicated by the dashed area 21. The horizontal line 22 shows the SLP for hypothetical (best) CoFe nanoparticles exhibiting a rectangular hysteresis loop operated at the biological discomfort level $Hf = 5 \cdot 10^9$ $Am^{-1}s^{-1}$ providing about 5900 W/g. Thus, also tumors of very small sizes are available for hyperthermia treatment with these particles.

The shaded rectangle 23 indicates tumors with a diameter of about 1 mm that can be treated with best CoFe nanoparticles with a particle concentration of 100 mg/cm³ that can be obtained by direct injection of the particles into the tumor. Magnetic nanoparticle concentrations of 10-100 mg/cm³ per tumor tissue are practicable. The shaded area 24 highlights the minimal diameter of tumors accessible with particle concentrations of 1 mg/cm³ of the best CoFe particles that can be expected for an antibody-targeted approach.

The invention claimed is:

1. A synthetic antiferromagnet disk-shaped particle comprising
    a first ferromagnetic layer,
    a second ferromagnetic layer,
    a non-magnetic interlayer arranged between the first and the second ferromagnetic layer, wherein each of the first and the second ferromagnetic layer comprises a uniaxial magnetic anisotropy in the plane of the ferromagnetic layers such that the switching fields from an antiferromagnetic alignment of the first and the second ferromagnetic layer to a ferromagnetic alignment ($H_{AF \to F}$) and from the ferromagnetic alignment to the antiferromagnetic alignment ($H_{F \to AF}$) fulfill the condition $H_{AF \to F} - H_{F \to AF} > \frac{1}{4} \cdot H_{AF \to F}$; wherein the uniaxial magnetic anisotropy in the plane of the ferromagnetic layers is larger than 5000 Joule per cubic meter; and wherein the synthetic antiferromagnet disk-shaped particle is characterized by a magnetic easy axis hysteresis loop in externally applied magnetic fields of 140 Millitesla or smaller.

2. The synthetic antiferromagnet disk-shaped particle according to claim 1, wherein an easy axis magnetic hysteresis loop has a substantially rectangular shape in the first and third quadrant of a coordinate system of magnetization versus magnetic field.

3. The synthetic antiferromagnet disk-shaped particle according to claim 1, wherein a ferromagnetic alignment of the first and the second ferromagnetic layers remains after the externally applied magnetic field is removed, but then decays back into an antiferromagnetically aligned ground state by thermal activation occurring at room temperature within a time period shorter than ten seconds; or the antiferromagnetically aligned ground state is re-established by application of an oscillatory magnetic field with a decaying field amplitude.

4. The synthetic antiferromagnet disk-shaped particle according to claim 1, wherein any one of the first or second ferromagnetic layer comprises Fe, Co, or Ni.

5. The synthetic antiferromagnet disk-shaped particle according to claim 4, wherein any one of the first or second ferromagnetic layer comprises an alloy comprising Fe, Co or Ni.

6. The synthetic antiferromagnet disk-shaped particle according to claim 5, wherein any one of the first or second ferromagnetic layer further comprises a rare earth element.

7. The synthetic antiferromagnet disk-shaped particle according to claim 6, wherein the rare earth element is samarium.

8. The synthetic antiferromagnet disk-shaped particle according to claim 4, wherein any one of the first or second ferromagnetic layer further comprises a rare earth element.

9. The synthetic antiferromagnet disk-shaped particle according to claim 8, wherein the rare earth element is samarium.

10. The synthetic antiferromagnet disk-shaped particle according to claim 1, wherein a diameter of the particle is between 10 nanometers and 5000 nanometers.

11. The synthetic antiferromagnetic disk-shaped particle according to claim 1, wherein a thickness of the particle is between 5 nanometers and 1000 nanometers.

12. The synthetic antiferromagnet disk-shaped particle according to claim 1, wherein the interlayer promotes an RKKY coupling between the first and the second ferromagnetic layer, thereby weakening the antiferromagnetic coupling between the first and the second ferromagnetic layer caused by magnetic stray fields of the first and second ferromagnetic layers.

13. The synthetic antiferromagnet disk-shaped particle according to claim 1, wherein the interlayer comprises platinum (Pt), iridium (Ir) or a PtIr alloy.

14. The synthetic antiferromagnet disk-shaped particle according to claim 13, wherein the interlayer comprises a $Pt_{1-x}Ir_x$ alloy.

15. The synthetic antiferromagnet disk-shaped particle according to claim 1, further comprising an additional layer capable of performing at least one of:
   oxidation protection of the first and the second ferromagnetic layer;
   chemical functionalization to obtain colloidal stability of the particle in liquids;
   biomedical functionalization;
   prevention of uptake of the particle by macrophages;
   release or reaction of a chemical substance comprised in the particle; and/or
   separation of the particle structure microfabricated on a substrate from the substrate.

16. The synthetic antiferromagnet disk-shaped particle according to claim 1, wherein the uniaxial magnetic anisotropy in the plane of the first ferromagnetic layer is generated through deposition of the first ferromagnetic layer onto an obliquely sputtered tantalum layer or through alloying the first ferromagnetic layer with a rare earth element.

* * * * *